United States Patent [19]

Teach

[11] Patent Number: 4,965,368
[45] Date of Patent: Oct. 23, 1990

[54] 5-OXY OR THIOMETHYL SUBSTITUTED OXAZOLIDINE HERBICIDE ANTIDOTES

[75] Inventor: Eugene G. Teach, El Cerrito, Calif.
[73] Assignee: ICI Americas Inc., Wilmington, Del.
[21] Appl. No.: 53,881
[22] Filed: May 26, 1987

Related U.S. Application Data

[60] Division of Ser. No. 564,980, Dec. 23, 1983, which is a division of Ser. No. 300,079, Sep. 8, 1981, abandoned, which is a continuation of Ser. No. 49,676, Jun. 18, 1979, abandoned.

[51] Int. Cl.$^5$ ............................................. C07D 263/02
[52] U.S. Cl. ......................................... 548/215; 71/88
[58] Field of Search .................................... 548/215

[56] References Cited

U.S. PATENT DOCUMENTS

| | | | |
|---|---|---|---|
| 3,959,304 | 5/1976 | Teach | 71/88 |
| 3,989,503 | 11/1976 | Pallos et al. | 71/88 |
| 4,021,224 | 5/1977 | Pallos et al. | 71/88 |
| 4,072,688 | 2/1978 | Teach | 71/88 |
| 4,249,931 | 2/1981 | Teach | 71/88 |

Primary Examiner—Richard L. Raymond
Assistant Examiner—E. J. Kraus
Attorney, Agent, or Firm—Denis A. Polyn

[57] ABSTRACT

N-haloacyl oxazolidines substituted in the 5-position with oxy or thio containing groups as new compositions of matter useful as active herbicidal antidotes to protect against and decrease crop injury when used with thiolcarbamate herbicides, and when applied in various methods; improved herbicidal compositions and utility of said compositions to protect against and decrease phytotoxic injury to crops when employing thiolcarbamate herbicides and a two-part herbicide system consisting essentially of a first-part of one or more thiolcarbamate herbicides and a second part of an effective antidote compound therefor, said antidote compounds of the class 3-haloacyl oxazolidine having the formula

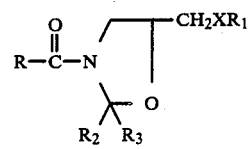

wherein X is selected from the group consisting of oxygen and sulfur; $R_1$ is selected from the group consisting of alkyl and alkenyl; R is selected from the group consisting of haloalkyl, alkylthio and p-tolylsulfonamido; $R_2$ and $R_3$ are independently selected from the group consisting of hydrogen and lower alkyl, each having 1 to 3 carbon atoms, inclusive; provided that the carbon content of $R_1 + R$ is less than or equal to 6 carbon atoms and further provided that when $XR_1$ is alkylthio, then R is other than haloalkyl having 3 to 4 carbon atoms, inclusive, and provided that when $XR_1$ is methoxy, R is other than 2,3-dibromopropyl; and in addition a compound selected from the group of compounds consisting of 2,2-dimethyl-3(3-bromopropionyl)5-pentoxymethyl oxazolidine; 2,2-dimethyl-3(5-chlorovaleryl)5-isopropoxymethyl oxazolidine; 2,2-dimethyl-3(5-chlorovaleryl)5-allyloxymethyl oxazolidine.

11 Claims, No Drawings

5-OXY OR THIOMETHYL SUBSTITUTED OXAZOLIDINE HERBICIDE ANTIDOTES

This is a divisional of application Ser. No. 564,980, filed Dec. 23, 1983, which in turn is a divisional of application Ser. No. 300,079, filed Sept. 8, 1981, now abandoned, which is a continuation of application Ser. No. 49,676, filed June 18, 1979, now abandoned.

BACKGROUND OF THE INVENTION

While many herbicides are immediately toxic to a large number of weed pests, it is known that the effect of many herbicides upon important plant cultivations is either non-selective or not adequately selective. Thus, many herbicides damage not only the weeds to be controlled, but to a greater or lesser extent, the desirable cultivated plants as well. This holds true for many herbicidal compounds which have been commercially successful and are commercially available. These herbicides include types such as triazines, urea derivatives, halogenated acetanilides, carbamates, thiolcarbamates and the like. Some examples of these compounds are described in U.S. Pat. Nos. 2,913,237, 3,037,853, 3,175,897, 3,185,720, 3,198,786, 3,582,314 and 3,952,056.

The side effect of injury to a cultivated crop by various herbicides is particularly inconvenient and unfortunate. When used in the recommended amounts in the soil to control broadleaf weeds and grasses, serious malformation or stunting of the crop plants sometimes result. This abnormal growth in the crop plants results in loss of crop yield. The search continues for good selective herbicides.

Previous attempts are described to overcome this problem. The treatment of the crop seed with certain "hormonal" antagonistic agents prior to planting is described; see U.S. Pat. Nos. 3,131,509 and 3,564,768. The protective agents, as well as the herbicide, in these prior processes are largely specific to certain cultivated plant species or in the nature of the antagonistic agents. The prior antagonistic agents have not been notably successful. The aforementioned patents specifically exemplify and describe the treatment of seeds employing compounds of a different chemical class, not suggestive of the present invention.

U.S. Pat. Nos. 3,989,503, 4,072,688 and 4,124,372 disclose certain substituted oxazolidine compounds. However, none of these references anticipate or make obvious the particular compounds or the utility of the particular compounds as herbicidal antidotes for thiolcarbamate herbicides, in particular for S-n-propyl N,N-di-n-propylthiolcarbamate, S-ethyl di-n-propyl thiolcarbamate, S-isopropyl 1-(5-ethyl-2-methylpiperidine) carbothioate, S-ethyl diisobuyl thiolcarbamate, and S-ethyl cyclohexyl ethyl thiolcarbamate. None of the references anticipate or make obvious the improved herbicidal compositions for use employing N-haloacyl oxazolidines substituted in the 5-position with substituted methyloxy or methylthio moieties.

DESCRIPTION OF THE INVENTION

It has been discovered that cultivated crop plants can be protected against injury by thiolcarbamate-type herbicides, and said injury can be decreased when the thiolcarbamate-type herbicides, each alone or in mixtures or combination with other compounds, are applied in a variety of ways. Further, as an alternative effect, the tolerance of the plants, to these herbicides, can be substantially increased by adding to the soil an antidote compound of the type N-haloacyl oxazolidine substituted in the 5-position with oxy or thio containing groups, therefore, the present invention also includes a two-part herbicide system comprising a first-part of one or more thiolcarbamate herbicides and a second-part of an effective antidote compound therefore, said antidote compounds corresponding to the following formula

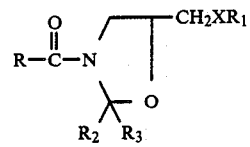

wherein X is oxygen or sulfur, $R_1$ is selected from the group consisting of alkyl and alkenyl; R is selected from the group consisting of haloalkyl and alkylthio; and $R_2$ and $R_3$ are independently selected from the group consisting of hydrogen and lower alkyl, provided that $R_1+R_2$ is less than or equal to 6 carbon atoms and further provided that when $XR_1$ is thioethyl, then R is other than haloalkyl having 3 or 4 carbons and provided that when $XR_1$ is methoxy, R is other than 2,3-dibromopropyl. Also, part of this invention are the specific compounds 2,2-dimethyl-3(3-bromopropionyl)5-pentoxymethyl oxazolidine; 2,2-dimethyl-3(5-chlorovaleryl)5-isopropoxymethyl oxazolidine; 2,2-dimethyl-3(5-chlorovaleryl)5-allyloxymethyl oxazolidine.

In the above description, the following embodiments are intended for the various substitutent groups: For $R_1$, alkyl preferably includes those members which contain from 1 to 6 carbon atoms, inclusive, in both straight chain and branched chain configurations. As exemplary of the alkyl portion within the preferred embodiment are the following: Methyl, ethyl, n-propyl, isopropyl, n-butyl, sec.-butyl, isobutyl, tert.-butyl, and n-hexyl; for $R_1$, alkenyl preferably includes those members which contain from 3 to 6 carbon atoms and at least one ethylenic or double bond such as in 1-propenyl, 2-butenyl, 3-butenyl, 1,1-dimethyl-3-butenyl, and the like. For $R_2$ and $R_3$ as lower alkyl, preferably includes those members which contains from 1 to 3 carbon atoms, inclusive; and for R as haloalkyl, preferably includes those members which contain from 1 to 5 carbon atoms, inclusive, and the term "halo" includes chloro, bromo and fluoro as mono, di, tri, tetra or hexa substitutions, that is from 1 to 6 halo substituents; and for R as alkylthio includes those members which contain from 1 to 4 carbon atoms, inclusive. Other substituent groups are as indicated in carbon content in the above description.

As an alternative mode of action, the compounds of this invention may interfere with the normal herbicidal action of the thiolcarbamate-type and other herbicides to render them selective in their action. The observation noted with the presence of the herein described antidote is a decrease in phytotoxicity with respect to various crops, otherwise observed when various thiolcarbamate herbicides are used for weed control. Whichever mode of action is present, the corresponding beneficial and desirable effect is the continued herbicidal effect of the thiolcarbamate against weed species present in the crop, with the accompanying decreased herbicidal effect on desired crop species. This advantage and utility will become more apparent hereinafter.

Therefore, the terms "antidote", "herbicide antidote" or "antidotal amount", is meant to describe that effect which tends to counteract the normal injurious herbicidal response that the herbicide might otherwise produce. Whether it is to be termed a remedy, interferant, protectant, antagonist or the like, will depend upon the mode of action. The mode of action is varied, but the effect, which is desirable, is the result of the method of treating the seed, soil or furrow in which a crop is planted.

The compounds of this invention represented by the above formulas can be prepared by several different procedures depending upon the starting materials.

When X is oxygen and $R_1$ is alkyl or alkenyl, the requisite starting material for the compounds within this invention may be prepared by amination of a 1,2-epoxy-3-alkoxy or alkenoxy propane (I) with aqueous ammonia or ammonium hydroxide to produce a 1-amino-3-alkoxy or alkenoxy-2-propanol (II). Subsequent reaction and cyclization with acetone or other aldehyde ketone (III) yields the N-unsubstituted 2,2-dialkyl 5-alkoxy or alkenoxy methyl oxazolidine product (IV). This sequence or reactions is depicted by the following equations:

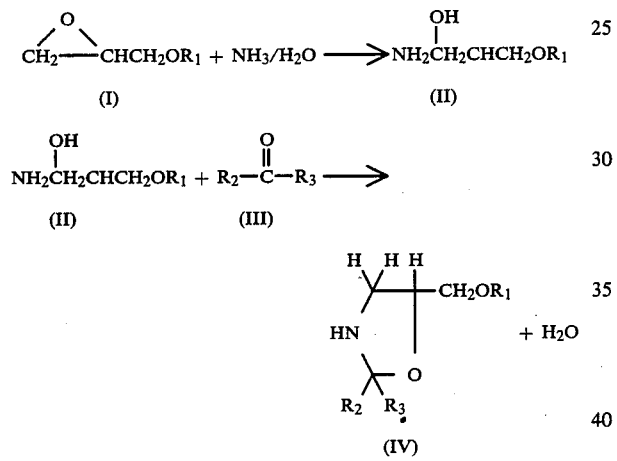

wherein $R_1$, $R_2$ and $R_3$ have the same significance as previously defined.

When X is sulfur and $R_1$ is alkyl or alkenyl, the requisite starting material for the compounds within this invention may be prepared by thionation with a mercaptan (VI) of epichlorohydrin (V) to produce the 1-chloro alkyl or 1-chloro alkenyl thio-2-propanol (VII), this is followed by reformation of the epoxide (VIII). Amination of the 1,2-epoxy-2-alkylthio or alkenylthio propane (VIII) with ammonia or aqueous ammonia produced a 1-amino-3-alkylthio or alkenylthio-2-propanol (IX). Subsequent reaction and cyclization with acetone or other aldehyde ketone (III) yields the N-unsubstituted 2,2-dialkyl-5 alkylthio or alkenylthio methyl oxazolidine product (X), this sequence of reactions is depicted by the following equations:

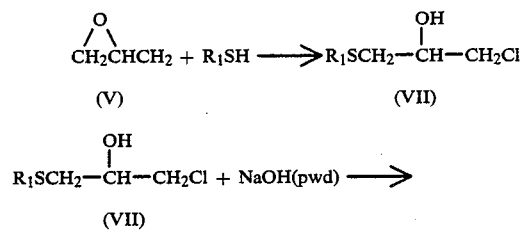

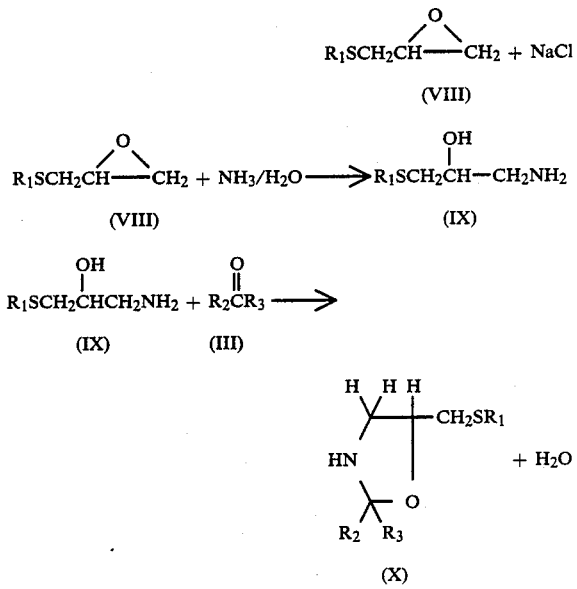

(a) The N-acyl-substituted compounds of the invention wherein R is haloalkyl, may be prepared by direct acylation of a 5-substitution oxazolidine compound with an acid chloride in the presence of a hydrogen chloride acceptor, such as triethylamine or an inorganic base, such as sodium hydroxide.

(b) The thiocarbamyl 3-substituted compounds of the invention wherein R is alkylthio may be prepared by direct alkylthio formylation of a 5-substituted oxazolidine compound with an alkylchlorothioformate in the presence of an acid chloride acceptor.

(c) The p-toluene sulfonylcarbamyl 3-substituted compounds of the invention wherein R is p-toluene sulfonyl may be prepared by direct carbamylation of a 5-substituted oxazolidine compound with p-toluene sulfonyl isocyanate.

In each reaction (a), (b) and (c), the reaction is performed in the presence of an inert organic solvent, such as benzene where good chemical practice dictates a catalyst was used as specified. In some instances, a catalyst is not required. The reaction temperatures can vary from $-10°$ C. to $90°$ C. The reaction pressure may be atmospheric, subatmospheric or superatmospheric. However, for convenience of conducting the reactions, the pressure is generally atmospheric. The reaction time will, of course, vary depending upon the reactants and reaction temperature. Generally, the reaction time is from 0.25 to 24 hours. After the reaction is complete, the product is recovered by separation and the solvent evaporated. The structure is confirmed by nuclear magnetic resonance or infrared spectra.

Whereas, solvent is normally employed to facilitate the reaction and aid in the work-up of the product after filtration, extraction and drying, the product can be purified further by trituration with hexane or recrystallization from a suitable solvent. In most instances, the structure was confirmed by analytical techniques such as infrared spectroscopy, nuclear magnetic resonance, or mass spectroscopy.

Representative of the above general scheme of reactions, are the following intermediate preparations employing specific sulfur containing starting materials and intermediates.

PREPARATION OF INTERMEDIATE

1-Chloro-3-ethylthio-2-propanol

Sixty five and two tenths (65.2) grams of ethyl mercaptan was added dropwise with stirring to 92.5 grams of epichlorohydrin and 2 grams of zinc chloride in 500 milliliters of dioxane. The mixture was heated to 40° C. and the heating removed while the mixture remained at 35°–40° C. for ¾ hour. The mixture was then heated at 40° C. for 1½ hour and then to reflux at which point the temperature was 105° C. Yield after stripping was 103 grams, $n_D^{30}1.4862$. The product was confirmed by infrared and nuclear magnetic resonance.

PREPARATION OF INTERMEDIATE

3-Ethyl-1,2-epoxypropyl sulfide

One hundred and twenty seven (127.0) grams of 1-chloro-3-ethylthio-2-propanol was added dropwise with vigorous stirring to 82 grams of powdered NaOH in 500 milliliters of diethyl ether. The temperature was kept below 30° C. with a water bath and addition took 40 minutes. The product was filtered and the ether stripped off giving 80.8 grams of product, $n_D^{30}1.4567$. The structure was confirmed by infrared and nuclear magnetic resonance and used in subsequent reactions without purification.

PREPARATION OF INTERMEDIATE

2-Hydroxy-3-aminopropyl ethyl sulfide

Eighty seven and eight tenths (87.8) grams of 3-ethyl-1,2-epoxypropyl sulfide was added dropwise with stirring to 1 liter of aqueous 28% ammonia solution, cooled to 0° C. overnight in an icebox, and maintained in an ice bath. The epoxide was added over 45 minutes and the reaction mixture was allowed to warm to room temperature stand in the hood overnight. The water and ammonia were stripped off under vacuum and the oily residue distilled to give 59.1 grams of the title compound; p.b. 101°–105° C. at 1.5–2 millimeters, $n_D^{30}1.4910$. The structure was confirmed by infrared and nuclear magnetic resonance.

In preparing the oxazolidine intermediates it was found that it was unnecessary to isolate and purify the compounds before use. The volume of the oxazolidine solution was adjusted to give a 25 percent w/v solution (4 milliliters=1 gram) and aliquots were then used for subsequent reactions. Both the 5-oxymethyl and 5-thiomethyl substituted oxazolidines can be prepared by similar reactions.

PREPARATION OF INTERMEDIATE

1-Amino-3-isopropoxy isopropanol

Sixty-three (63.0) grams of 3-isopropoxy-1,2-epoxy propane was added dropwise with stirring to 1 liter of 28 percent aqueous ammonia, cooled to 0° C., and kept in an icebox overnight. The solution was allowed to warm to room temperature and stored in a loosely stoppered container for five days in a hood. The water and ammonia was stripped off under vacuum and the oily residue distilled to give 38 grams of the title compound; b.p. 77.5° C. at 0.5 millimeters, $n_D^{30}1.4200$. The structure was confirmed by infrared and nuclear magnetic resonance.

PREPARATION OF INTERMEDIATE

2,2-Dimethyl-5-isopropoxymethyl oxazolidine

Twenty six and six tenths (26.6) grams of 1-amino-3-isopropoxy isopropanol and 12 grams of acetone were added to 150 milliliters of benzene and heated to reflux under a modified Dean Stark apparatus. When about 4 milliliters of water had been azeoropically removed, an additional 20 milliliters of benzene was distilled off and the mixture allowed to cool to room temperature. The volume was adjusted to 138.4 milliliters with benzene to give a 25 percent w/v solution of the title compound. Aliquots of this solution were used to prepare several of the subject compounds.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE I

Preparation of 2,2-dimethyl-N-trichloroacetyl-5-isopropoxymethyl oxazolidine.

To 20.8 milliliters of 25 percent w/v, 2,2-dimethyl-5-isopropoxymethyl oxazolidine solution in 50 milliliters of benzene was added 5.5 grams of trichloroacetyl chloride. To this solution was added dropwise with cooling, 3.1 grams of trimethylamine. After washing with water, drying and removal of the benzene in vacuo, there was obtained 8.1 grams of the title compound, $n_D^{30}1.4603$. Analytical data supports the structure.

EXAMPLE II

Preparation of 2,2-dimethyl N-dichloroacetyl-5-isopropoxymethyl oxazolidine.

In a similar manner as Example I, 27.7 milliliters of 25 percent w/v, 2,2-dimethyl-5-isopropoxymethyl oxazolidine solution in 50 milliliters of benzene and 4.9 grams of dichloroacetyl chloride was added 4.1 grams of triethylamine. After the appropriate work up procedure, there was obtained a yield of 8.9 grams, $n_D^{30}1.4564$. Analytical data supports the structure.

EXAMPLE II

Preparation of 2,2-dimethyl-3-(p-toluene-sulfonyl carbamyl)5-isopropoxymethyl oxazolidine.

To 20.8 milliliters of 25 percent w/v, 2,2-dimethyl-5-isopropoxymethyl oxazolidine solution in 50 milliliters of benzene was added 5.9 grams of p-toluene sulfonyl isocyanate. Upon completion of the reaction the solvent, benzene, was removed in vacuo. There was obtained 12.8 grams of the title compound, as a glass. Analytical data supports the structure.

EXAMPLE IV

Preparation of 2,2-dimethyl-3-(2,3-dibromopropionyl)-5-methoxymethyl oxazolidine.

To 11.6 milliliters of 25 percent w/v, 2,2-dimethyl-5-methoxymethyl oxazolidine solution in 50 milliliters of benzene with 5.0 grams of 2,3-dibromopropionyl chloride was added dropwise 2.1 grams of triethylamine.

After the reaction was complete the mixture was washed with water, separated, dried and the organic solvent removed in vacuo. There was obtained 2.7 grams of the title compound, $n_D^{30}1.4887$. Analytical data supports the structure.

EXAMPLE V

Preparation of 2,2-dimethyl-3-dichloroacetyl-5-allyloxymethyl oxazolidine.

To a reaction mixture of 25 percent w/v, 34.2 milliliters of 2,2-dimethyl-5-allyloxymethyl oxazolidine solution in 100 milliliters benzene with 4 grams of 50% sodium hydroxide solution, was added dropwise, 7.4 grams of dichloroacetyl chloride. Cooling in an ice bath and vigorous stirring was maintained during the addition of the chloride. Upon completion of the reaction the mixture was washed with water, dried, separated and the organic solvent removed in vacuo. There was obtained 10.0 grams of the title compound, $n_D^{30}1.4705$. Analytical data supports the structure.

EXAMPLE VI (a-c)

(a) Preparation of 2,2-dimethyl-3-chloroacetyl-5-ethylthiomethyl oxazolidine.

To 21 milliliters of 25 percent w/v, 2,2-dimethyl-5-ethylthiomethyl oxazolidine solution in 25 milliliters of benzene was added dropwise 3.4 grams of chloroaceyl chloride. While cooling in an ice bath and with vigorous stirring, the further dropwise addition of 3.1 grams of triethylamine was carried out. The reaction mixture was allowed to stir for about 1 hour. At the end of this time the mixture was washed with water, separated, dried and the organic solvent removed in vacuo. There was obtained 6.2 grams of the title compound, $n_D^{30}1.4942$. Infrared data supports the structure.

(b) Preparation of 2,2-dimethyl-3-ethylthiocarbamyl-5-ethylthiomethyl oxazolidine.

To 19.3 milliliters of 25 percent w/v, 2,2-dimethyl-5-ethylthiomethyl oxazolidine solution in 25 milliliters of benzene was added 2.9 grams of triethylamine and 3.4 grams of ethylchlorothiolformate as in the procedure for (a) supra. Work-up was similar to (a). There was obtained a yield of 7.1 grams of the title compound, $n_D^{30}1.4940$. Infrared data supports the structure.

(c) Preparation of 2,2-dimethyl-3-dichloroacetyl-5-ethylthiomethyl oxazolidine.

To 52.5 milliliters of 25 percent w/v, 2,2-dimethyl-5-ethylthiomethyl oxazolidine solution in 100 milliliters of benzene was added 6.5 grams of 50% solution of sodium hydroxide (10% excess) was added 12.1 grams of dichloroacetyl chloride dropwise. The reaction mixture was cooled in an ice bath with vigorous stirring during the dropwise addition. The temperature was maintained at below 10° C. during the addition and allowed to stir about 30 minutes at room temperature. The work-up procedure was similar to (a) supra. There was obtained a yield of 15.3 grams of the title compound, $n_D^{30}1.4980$.

TABLE I $$\begin{array}{c} \text{O} \\ \| \\ \text{R}-\text{C}-\text{N} \end{array} \underset{\text{R}_2 \quad \text{R}_3}{\overbrace{\phantom{XXXX}}^{\text{CH}_2\text{XR}_1}} \text{O}$$

| Compound Number | R | $XR_1$ | $R_2$ | $R_3$ | Physical Constant ($n_D^{30}$) |
|---|---|---|---|---|---|
| 1 | $CCl_3$ | $OCH(CH_3)_2$ | $CH_3$ | $CH_3$ | 1.4603 |
| 2 | $CHCl_2$ | $OCH(CH_3)_2$ | $CH_3$ | $CH_3$ | 1.4564 |
| 3 | $CH_2Cl$ | $OCH(CH_3)_2$ | $CH_3$ | $CH_3$ | 1.4488 |
| 4 | $CH_3CHBrCHBr$ | $OCH(CH_3)_2$ | $CH_3$ | $CH_3$ | 1.4722 |
| 5 | $CH_3\phi SO_2NH$ | $OCH(CH_3)_2$ | $CH_3$ | $CH_3$ | (Glass) |
| 6 | $CHCl_2$ | $OCH_3$ | $CH_3$ | $CH_3$ | 1.4730 |
| 7 | $CH_2BrCHBr$ | $OCH_3$ | $CH_3$ | $CH_3$ | 1.4887 |
| 8 | $C_3H_7S$ | $OCH_3$ | $CH_3$ | $CH_3$ | 1.4620 |
| 9 | $CHCl_2$ | $OC_2H_5$ | $CH_3$ | $CH_3$ | 1.4610 |
| 10 | $CH_2BrCH_2$ | $OC_2H_5$ | $CH_3$ | $CH_3$ | 1.4620 |
| 11 | $CH_2BrCHBr$ | $OC_2H_5$ | $CH_3$ | $CH_3$ | 1.4998 |
| 12 | $CHCl_2$ | $OCH_2CH=CH_2$ | $CH_3$ | $CH_3$ | 1.4705 |
| 13 | $CH_2BrCHBr$ | $OCH_2CH=CH_2$ | $CH_3$ | $CH_3$ | 1.4934 |
| 14 | $CH_2BrCH_2$ | $OCH_2CH=CH_2$ | $CH_3$ | $CH_3$ | 1.4764 |
| 15 | $CH_2ClCH_2$ | $OCH_2CH=CH_2$ | $CH_3$ | $CH_3$ | 1.4602 |
| 16 | $CH_3CHCl$ | $OCH_2CH=CH_2$ | $CH_3$ | $CH_3$ | 1.4562 |
| 17 | $CHCl_2$ | $OC_3H_7$ | $CH_3$ | $CH_3$ | 1.4560 |
| 18 | $CH_2BrCHBr$ | $OC_3H_7$ | $CH_3$ | $CH_3$ | 1.4795 |
| 19 | $CH_2BrCH_2$ | $OC_3H_7$ | $CH_3$ | $CH_3$ | 1.4612 |
| 20 | $CH_2ClCH_2$ | $OC_3H_7$ | $CH_3$ | $CH_3$ | 1.4470 |
| 21 | $CHCl_2$ | $OC_4H_9$ | $CH_3$ | $CH_3$ | 1.4557 |
| 22 | $CH_2BrCHBr$ | $OC_4H_9$ | $CH_3$ | $CH_3$ | 1.4788 |
| 23 | $CH_2BrCH_2$ | $OC_4H_9$ | $CH_3$ | $CH_3$ | 1.4583 |
| 24 | $CH_2ClCH_2$ | $OC_4H_9$ | $CH_3$ | $CH_3$ | 1.4462 |
| 25 | $CH_3CHCl$ | $OC_4H_9$ | $CH_3$ | $CH_3$ | 1.4420 |
| 26 | $CH_2Cl(CH_2)_3$ | $OCH_3$ | $CH_3$ | $CH_3$ | 1.4588 |
| 27 | $CH_2ClCHBr$ | $OCH_3$ | $CH_3$ | $CH_3$ | 1.4808 |
| 28 | $CH_2ClCHBr$ | $OCH(CH_3)_2$ | $CH_3$ | $CH_3$ | 1.4692 |
| 29 | $CHCl_2$ | $OC_5H_{11}$ | $CH_3$ | $CH_3$ | 1.4508 |
| 30 | $CH_2BrCHBr$ | $OC_5H_{11}$ | $CH_3$ | $CH_3$ | 1.4773 |
| 31 | $CH_2BrCH_2$ | $OC_5H_{11}$ | $CH_3$ | $CH_3$ | 1.4568 |

TABLE I-continued

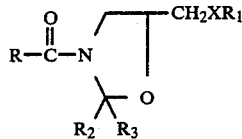

| Compound Number | R | XR$_1$ | R$_2$ | R$_3$ | Physical Constant ($n_D^{30}$) |
|---|---|---|---|---|---|
| 32 | CH$_2$Cl | SC$_2$H$_5$ | CH$_3$ | CH$_3$ | 1.4942 |
| 33 | CH$_2$BrCHBr | SC$_2$H$_5$ | CH$_3$ | CH$_3$ | 1.5142 |
| 34 | CH$_2$BrCH$_2$ | SC$_2$H$_5$ | CH$_3$ | CH$_3$ | 1.4973 |
| 35 | CH$_2$ClCH$_2$ | SC$_2$H$_5$ | CH$_3$ | CH$_3$ | 1.4862 |
| 36 | C$_2$H$_5$S | SC$_2$H$_5$ | CH$_3$ | CH$_3$ | 1.4940 |
| 37 | CHCl$_2$ | SC$_2$H$_5$ | CH$_3$ | CH$_3$ | 1.4980 |
| 38 | CH$_2$Cl(CH$_2$)$_3$ | OCH$_3$ | CH$_3$ | CH$_3$ | 1.4545 |
| 39 | CH$_2$Cl(CH$_2$)$_3$ | OC$_2$H$_5$ | CH$_3$ | CH$_3$ | 1.4509 |
| 40 | CH$_2$Cl(CH$_2$)$_3$ | OC$_3$H$_7$ | CH$_3$ | CH$_3$ | 1.4463 |
| 41 | CH$_2$Cl(CH$_2$)$_3$ | OCH(CH$_3$)$_2$ | CH$_3$ | CH$_3$ | 1.4476 |
| 42 | CH$_2$Cl(CH$_2$)$_3$ | OCH$_2$CH=CH$_2$ | CH$_3$ | CH$_3$ | 1.4586 |
| 43 | CH$_2$Cl(CH$_2$)$_3$ | OC$_4$H$_9$ | CH$_3$ | CH$_3$ | 1.4500 |
| 44 | C$_5$H$_{11}$CHBrCHBr | OC$_2$H$_5$ | CH$_3$ | CH$_3$ | 1.4682 |
| 45 | C$_5$H$_{11}$CHBrCHBr | SC$_2$H$_5$ | CH$_3$ | CH$_3$ | 1.4942 |
| 46 | C$_3$H$_7$CHBr | OC$_3$H$_7$ | CH$_3$ | CH$_3$ | 1.4563 |

The herbicidal compound employed in the utility of this invention is an active thiolcarbamate herbicide of a general type. That is, it is a member of the class of herbicidally active compounds effective against a wide range of plant species, and may have no discrimination between desirable and undesirable plant species. The method of controlling vegetation comprises applying a herbicidally effective amount of the herein described herbicidal composition to the area, plant or plant locus where control is desired. The herbicidal composition as set forth in this invention include those wherein the antidote is as described above and the preferred active herbicidal compound is selected from the class of thiolcarbamate herbicides and includes the following representative members: S-ethyl dipropyl thiolcarbamate, S-ethyl diisobutyl thiolcarbamate, S-propyl di-n-propyl thiolcarbamate, S-ethyl cyclohexyl ethyl thiolcarbamate, S-ethyl hexahydro-1H-azepine-1 carbothioate, 2,3,3-trichloroallyl N,N-diisopropyl thiolcarbamate, S-isopropyl-1-(5-ethyl-3-methylpiperidine) carbothioate and S-4-chlorobenzyl diethyl thiolcarbamate.

As an embodiment within the scope of the present invention is a two-part or package herbicide system comprising a first-part of one or more thiolcarbamate herbicides and a second-part of an antidote compound therefor. It is understood that the antidote compound is used in an effective amount to render the two-part herbicide system selective in decreasing phytotoxic effects to desired or beneficial crops and yet phytotoxic to the undesirable or unwanted vegetation. Thus, the soil treated by such a system becomes extremely useful and desirable, allowing previously injured crops to be planted in said treated soil, otherwise injured by the herbicide when used alone. Hence, soil treated with herbicide and antidote as described herein is beneficial, desirable and useful.

An herbicide as used herein means a compound which controls or modifies the growth of vegetation or plants. Such controlling or modifying effects include all deviations from natural development; for example, killing, retardation, defoliation, desiccation regulation, stunting, tillering, stimulation, dwarfing and the like. By "plants", it is meant germinant seeds, emerging seedlings and established vegetation including the roots and above-ground portions.

Evaluation Procedure and Method

Flats to be used for growing the crops and weed species were filled with loamy sand soil. Various methods of application were employed, such as pre-plant incorporation (PPI) of (1) the herbicide and antidote separately, and (2) as a tank mix (PPI-TM) with the herbicide and antidote together. The application was by incorporation, whereinafter the seeds of the crops and weeds were planted in the treated soil; application by an in-furrow (IF) treatment of the seeds and surrounding soil in which the herbicide had been applied previously to the soil; and treatment of the crop seeds (ST) with an antidote candidate prior to planting in herbicide treated soil; application to the surface of the soil prior to emergence of the growing plants (1) as separate application (PES) of herbicide or antidote and (2) as a tank mix (PES-TM).

Stock solutions of representative thiolcarbamate herbicides and antidote candidates were prepared as follows:

Herbicides

A. S-ethyl di-n-propyl thiolcarbamate-EPTC-EPTAM ®6E-4133 mg. dissolved in 800 ml. water such that 5 ml. applied to the soil from a planting flat is equivalent to 5 lb/A PPI or 3744 mg. dissolved in 600 ml. of water, 5 ml. of which was equivalent to 6 lb/A PPI.

B. S-isopropyl 1-(5-ethyl)-2-methyl-piperidine) carbothioate (R-12001) technical, the following is a listing of various stock solutions prepared, also included is the lb/A equivalence per 5 ml. pre-plant incorporated.

120 mg/150 ml acetone; 5 ml=1 lb/A PPI
 176 mg/150 ml acetone; 5 ml=1.5 lb/A PPI
 117 mg/175 ml acetone; 5 ml=2 lb/A PPI
 975 mg/250 ml acetone; 5 ml=5 lb/A PPI
 585 mg/125 ml acetone; 5 ml=6 lb/A PPI C. S-ethyl di-isobutyl thiolcarbamate -SUTAN ® 6E or S-ethyl cyclohexyl ethyl thiolcarbamate-RONEET ® 6E-390 mg. dissolved in 125 ml. water such that 5 ml. applied to the soil from a planting flat is equivalent to 3 lb/A. For 4 lb/A 1456 mg. was dissolved in 350 ml. water, such that 5 ml. was equivalent to the desired amount.

D. S-ethyl hexahydro-1H-azepine-1-carbothioate ORDRAM® 8E-164 mg. dissolved in 75 ml. water such that 5 ml. is equivalent to 2 lb/A applied to the soil from a planting flat pre-plant incorporated.

E. S-propyl di-n-propyl thiolcarbamate-VERNAM®-6E (80%), the following is a listing of various stock solutions prepared, also included is the lb/A equivalence for 5 ml. pre-plant incorporated:

122 mg/125 ml H$_2$O; 5 ml=1 lb/A PPI
183 mg/150 ml H$_2$O; 5 ml=1.25 lb/A PPI
975 mg/250 ml H$_2$O; 5 ml=4 lb/A PPI
2632 mg/450 ml H$_2$O; 5 ml=6 lb/A PPI
3412 mg/500 ml H$_2$O; 5 ml=7 lb/A PPI

Antidotes

F. For each candidate compound employed in the seed treatment method of application, 250 mg. active ingredient was dissolved in 2.5 ml. acetone, with 1% Tween 20 ® (polyoxyethylene sorbitan monolaurate) such that 0.5 ml. of solution per 10 gm. of seeds is equal to ½% w/w.

G. For each candidate compound employed in the "in-furrow" method of application, 95 mg. of active ingredient was dissolved in 15 ml. of acetone with 1% Tween 20 ®, such that 1.5 ml. applied to the seed and soil in the furrow, in one-half of the flat was equivalent to 5 lb/A. When 1.0 lb/A is desired 0.3 ml. was used.

H. For each candidate compound employed in the "tank mix" pre-plant incorporation test or separately applied pre-plant incorporated test, 50 mg. of active ingredient was dissolved in 100 ml. of acetone with 1% Tween 20 ®, such that when 10 ml. of the stock solution was further dissolved in 90 ml. of acetone, 4 ml. was equivalent to 1/20 lb/A PPI. When 39 mg. of the compound was dissolved in 10 ml. of acetone, 5 ml. was equivalent to 5 lb/A PPI, and 1 ml. was equivalent to 1 lb/A PPI. When 16 mg. was dissolved in 20 ml., 10 ml. was equivalent to 2 lb/A PPI and when 16 mg. was dissolved in 40 ml., 5 ml. was equivalent to 0.5 lb/A PPI.

In-furrow application of the antidote employed the above stock solutions. As a preparatory step, a one pint sample of soil was removed from each flat to be retained and used later to cover the seeds after treatment with the stock solutions. The soil was leveled before planting. The herbicide stock solution was applied respectively to separate flats and pre-plant incorporated in the soil from the planting flat at the equivalent rate of 1 lb/A active ingredient or the indicated rate.

Rows ¼-inch deep were made lengthwise in each treated flat preparatory to seeding. After seeding, the flats were sectioned into two equal portions using a wooden barrier and 1-½ milliliters of additive stock solution I was atomized directly onto the exposed seed and soil in the open furrow in one-half of the flat. The untreated section of the flat served as an herbicide check and also made it possible to observe any lateral movement of the antidote through the soil. The seeds were covered with the one pint sample of untreated soil which had been removed earlier.

For tank mixes to be applied as a pre-plant incorporated application, the following solutions and procedures were employed. Five milliliters (5 ml.) of herbicide stock solutions were each mixed with five milliliters (5 ml.) of antidote candidate stock solution such that the equivalent of 1 lb/A and 5 lb/A of herbicide and antidote, respectively, were applied and incorporated into the soil of each flat. For pre-plant incorporation, the mixed stock solutions were injected into the soil during incorporation in a 5-gallon rotary mixer. Other stock solutions were employed at indicated rates in the tank mix procedure.

In side-by-side tests with various weed species and crops, it was found that weed control was maintained while at the same time the crop species were protected or injury decreased, when compared to a check or control flat. The control flat contained no candidate antidote compound. The following table includes those results.

For seed treatment, 10 grams of seed in a suitable container was shaken with 0.5 milliliters of antidote stock solution H, or other stock solution as indicated, such that the seed treatment was equivalent to 0.5% w/w, 0.25% w/w, 0.125% w/w or 0.1% w/w. Shaking was continued until the seeds were uniformly covered. The antidote compounds may be applied as liquid slurries and powder or dust treatments. The treated seeds were planted in soil in which herbicide stock solution had been pre-plant incorporated into the soil at a rate equivalent to 1 lb/A active ingredient.

All flats were placed on greenhouse benches where temperatures were maintained between 70°–90° F. The soil was watered by sprinkling to assure good plant growth. Injury ratings were taken 2 and 4 weeks after the applications were made. Individual control flats treated with the herbicide alone were included to provide a basis for determining the amount of injury reduction provided by the herbicide antidotes. The results of these tests are tabulated in Table II.

TABLE II

ANTIDOTE ACTIVITY

| Application Method: | |
|---|---|
| Seed Treatment | ST |
| In-Furrow | IF |
| Pre-Plant Incorporation | PPI |
| Pre-Plant Incorporation-Tank Mix | PPI-TM |
| Crop Species: | |
| Barley | BA [*Hordeum vulgare* (L.)] |
| Corn | CN [*Zea maize*] |
| Cotton | CT [*Gossypium hirsutum*] |
| Milo (Grain Sorghum) | MO [*Sorghum vulgare*] |
| Rice | RC [*Dryza sativa*] |
| Soybeans | SOY [*Glycine max*] |
| Wheat | WH [*Triticum aestivum*] |
| Weed Species: | |
| Green Foxtail | FT [*Setaria viridis*] |
| Johnson Grass | JG [*Sorghum halepense*] |
| Nutsedge | NS [*Cyperus esulentus*] |

TABLE II-continued

Shattercane     SC [*Sorghum bicolor*]
Watergrass     WG [*Echinochloa crusgalli*]
Wild Oats     WO [*Avena fatua* (L.)]

$$\text{Result} = \frac{\text{Percent injury with antidote present}}{\text{Percent injury of herbicide alone}}$$

| Compound Number | Herbicide PPI | Antidote Method of Application | Rate (Herb. + Anti.) (lbs/A or % ST.) | Crop | % Injury Result | Weed | Result |
|---|---|---|---|---|---|---|---|
| 1 | VERNAM | IF | 1 + 5 | CT | 40/70 | | |
| | | IF | 6 + 5 | CN | 0/70 | | |
| | VERNAM | PPI | 4 + 1 | SOY | 30/50 | WG | 100/100 |
| | | | | | | FT | 90/90 |
| | EPTAM | PPI-TM | 5 + 5 | CN | 0/80 | WG | 100/100 |
| | | | | | | FT | 100/100 |
| 2 | VERNAM | IF | 1 + 5 | MO | 50/95 | | |
| | | IF | 6 + 5 | CN | 0/70 | | |
| | ORDRAM | ST | 2 + 0.5% | MO | 10/70 | WG | 90/90 |
| | | | | | | SC | 70/70 |
| | RONEET | ST | 3 + 0.5% | MO | 10/70 | WG | 80/80 |
| | | | | | | SC | 80/80 |
| | EPTAM | PPI-TM | 5 + 0.05 | CN | 0/80 | WG | 100/100 |
| | | PPI-TM | 5 + 5 | CN | 0/80 | FT | 100/100 |
| | R-12001 | ST | 2 + 0.5% | MO | 50/90 | WG | 95/95 |
| | | | | | | SC | 95/95 |
| | RONEET | PPI-TM | 3 + 1 | MO | 10/80 | WG | 100/100 |
| | | | | | | FT | 100/100 |
| | | | 3 + 2 | MO | 0/80 | WG | 100/100 |
| | | | | | | FT | 100/100 |
| | | | 3 + 5 | MO | 0/80 | WG | 100/100 |
| | | | | | | FT | 100/100 |
| 3 | VERNAM | IF | 6 + 5 | CN | 10/70 | | |
| | RONEET | IF | 3 + 5 | MO | 40/75 | WG | 85/85 |
| | | | | | | SC | 95/95 |
| 4 | VERNAM | IF | 1 + 5 | WH | 40/70 | | |
| | | | | CT | 50/70 | | |
| | | | | RC | 30/95 | | |
| | | | | BA | 30/50 | | |
| | | | 6 + 5 | CN | 30/70 | | |
| | R-12001 | IF | 5 + 5 | CT | 0/50 | WG | 95/95 |
| | | | | | | FT | 95/95 |
| 5 | VERNAM | IF | 6 + 5 | SOY | 30/55 | | |
| | | IF | 4 + 1 | SOY | 20/50 | WG | 100/100 |
| | | | | | | FT | 100/100 |
| | RONEET | IF | 4 + 5 | MO | 30/60 | FT | 80/80 |
| | | | | | | JG | 100/100 |
| 6 | VERNAM | IF | 1 + 5 | MO | 50/95 | | |
| | | IF | 6 + 5 | CN | 0/90 | | |
| | EPTAM | PPI | 5 + 0.5 | CN | 0/80 | WG | 100/100 |
| | | | | | | FT | 100/100 |
| | | PPI | 5 + 5 | CN | 0/80 | WG | 100/100 |
| | | | | | | FT | 100/100 |
| | RONEET | IF | 4 + 5 | MO | 20/60 | FT | 80/80 |
| | | | | | | SC | 100/100 |
| | | PPI-TM | 3 + 1 | MO | 10/80 | WG | 100/100 |
| | | | | | | FT | 100/100 |
| | | | 3 + 5 | MO | 0/80 | WG | 100/100 |
| | | | | | | FT | 100/100 |
| 7 | VERNAM | IF | 1 + 5 | WH | 50/75 | | |
| | | IF | 6 + 5 | CN | 0/90 | | |
| | EPTAM | PPI | 5 + 0.5 | CN | 0/80 | WG | 100/100 |
| | | | | | | FT | 100/100 |
| | | PPI | 5 + 5 | CN | 0/80 | WG | 100/100 |
| | | | | | | FT | 100/100 |
| 8 | VERNAM | IF | 1 + 5 | RC | 30/95 | | |
| 9 | VERNAM | IF | 1.25 + 5 | MO | 10/100 | | |
| | | IF | 1.25 + 5 | BA | 40/95 | | |
| | | IF | 6 + 5 | CN | 20/85 | | |
| | RONEET | IF | 3 + 1 | MO | 40/90 | WG | 95/95 |
| | | | | | | SC | 100/100 |
| | EPTAM | PPI | 5 + 5 | CN | 0/80 | WG | 100/100 |
| | | | | | | FT | 100/100 |
| 10 | VERNAM | IF | 1.25 + 5 | MO | 50/100 | | |
| | | | 6 + 5 | CN | 0/85 | | |
| | RONEET | IF | 3 + 5 | MO | 30/90 | WG | 95/95 |
| | | | | | | SC | 100/100 |
| | EPTAM | PPI | 5 + 0.5 | CN | 0/80 | WG | 100/100 |
| | | | | | | FT | 100/100 |
| 11 | VERNAM | IF | 1.25 + 5 | BA | 30/95 | | |
| 12 | VERNAM | IF | 1.25 + 5 | MO | 30/100 | | |
| | | IF | 1.25 + 5 | BA | 30/90 | | |
| | | IF | 6 + 5 | CN | 0.90 | | |

TABLE II-continued

| | | | | | | | |
|---|---|---|---|---|---|---|---|
| | EPTAM | PPI | 5 + 0.5 | CN | 0/95 | FT | 100/100 |
| | | | | | | WO | 100/100 |
| | RONEET | PPI | 3 + 1 | MO | 10/90 | WG | 100/100 |
| | | | | | | SC | 100/100 |
| 13 | VERNAM | IF | 1.25 + 5 | BA | 30/90 | | |
| | | IF | 6 + 5 | CN | 0/90 | | |
| | EPTAM | PPI | 5 + 5 | CN | 0/80 | WG | 100/100 |
| | | | | | | FT | 100/100 |
| 14 | VERNAM | IF | 6 + 5 | CN | 0/90 | | |
| | | IF | 6 + 5 | SOY | 20/50 | | |
| | EPTAM | PPI | 5 + 0.5 | CN | 0/80 | WG | 100/100 |
| | | | | | | FT | 100/100 |
| 15 | VERNAM | IF | 6 + 5 | CN | 0/90 | | |
| | EPTAM | PPI | 5 + 5 | CN | 0/80 | WG | 100/100 |
| | | | | | | FT | 100/100 |
| 16 | VERNAM | IF | 6 + 5 | CN | 50/90 | | |
| 17 | VERNAM | IF | 1.25 + 5 | MO | 30/100 | | |
| | | IF | 6 + 5 | CN | 0/90 | | |
| | EPTAM | PPI | 5 + 5 | CN | 0/80 | WG | 100/100 |
| | | | | | | FT | 100/100 |
| | RONEET | PPI | 3 + 2 | MO | 10/90 | WG | 100/100 |
| | | | | | | SC | 100/100 |
| 18 | VERNAM | IF | 6 + 5 | CN | 0/90 | | |
| | | IF | 1.25 + 5 | WH | 60/95 | | |
| | | IF | 1.25 + 5 | BA | 60/90 | | |
| | EPTAM | PPI | 5 + 5 | CN | 0/80 | WG | 100/100 |
| | | | | | | FT | 100/100 |
| 19 | VERNAM | IF | 6 + 5 | CN | 0/90 | | |
| | EPTAM | PPI | 5 + 0.5 | CN | 0/80 | WG | 100/100 |
| | | | | | | FT | 100/100 |
| 20 | VERNAM | IF | 6 + 5 | CN | 0/90 | | |
| | EPTAM | PPI | 5 + 5 | CN | 0/80 | WG | 100/100 |
| | | | | | | FT | 100/100 |
| 21 | VERNAM | IF | 6 + 5 | CN | 0/90 | | |
| | EPTAM | PPI | 5 + 5 | CN | 0/80 | WG | 100/100 |
| | | | | | | FT | 100/100 |
| | RONEET | PPI-TM | 3 + 5 | MO | 0/80 | WG | 85/100 |
| | | | | | | FT | 100/100 |
| 22 | VERNAM | IF | 6 + 5 | CN | 0/90 | | |
| | EPTAM | PPI | 5 + 0.5 | CN | 0/80 | WG | 100/100 |
| | | | | | | FT | 100/100 |
| | VERNAM | IF | 1.25 + 5 | BA | 60/90 | | |
| 23 | VERNAM | IF | 6 + 5 | CN | 0/90 | | |
| | EPTAM | PPI | 5 + 5 | CN | 0/80 | WG | 100/100 |
| | | | | | | FT | 100/100 |
| 24 | VERNAM | IF | 6 + 5 | CN | 60/90 | | |
| 25 | VERNAM | IF | 6 + 5 | CN | 60/90 | | |
| 26 | VERNAM | IF | 1.25 + 5 | MO | 50/100 | | |
| | | IF | 6 + 5 | CN | 0/90 | | |
| | EPTAM | PPI | 5 + 5 | CN | 0/70 | WG | 100/100 |
| | | | | | | FT | 100/100 |
| | RONEET | PPI-TM | 3 + 5 | MO | 40/80 | WG | 100/100 |
| | | | | | | FT | 100/100 |
| 27 | VERNAM | IF | 1.25 + 5 | MO | 40/100 | | |
| | | IF | 1.25 + 5 | WH | 50/100 | | |
| | | IF | 1.25 + 5 | BA | 20/90 | | |
| | | IF | 6 + 5 | CN | 10/90 | | |
| | RONEET | PPI-TM | 3 + 5 | MO | 35/80 | WG | 100/100 |
| | | | | | | FT | 100/100 |
| | EPTAM | PPI | 5 + 5 | CN | 0/70 | WG | 100/100 |
| | | | | | | FT | 100/100 |
| 28 | VERNAM | IF | 1.25 + 5 | BA | 30/90 | | |
| | | IF | 6 + 5 | CN | 0/90 | | |
| | EPTAM | PPI | 5 + 5 | CN | 0/70 | WG | 100/100 |
| | | | | | | FT | 100/100 |
| | VERNAM | PPI-TM | 1.25 + 5 | WH | 30/80 | WG | 95/95 |
| 29 | VERNAM | IF | 6 + 5 | CN | 10/90 | | |
| | SUTAN | PPI-TM | 6 + 1 | CT | 30/50 | JG | 100/100 |
| | | | | | | NS | 90/90 |
| | EPTAM | PPI | 5 + 0.5 | CN | 0/70 | WG | 100/100 |
| | | | | | | FT | 100/100 |
| | RONEET | PPI-TM | 3 + 5 | MO | 15/80 | WG | 100/100 |
| | | | | | | FT | 100/100 |
| 30 | VERNAM | IF | 6 + 5 | CN | 70/90 | | |
| 31 | VERNAM | IF | 6 + 5 | CN | 40/90 | | |
| | | IF | 6 + 5 | SOY | 50/70 | | |
| 32 | VERNAM | IF | 6 + 5 | CN | 20/90 | | |
| | EPTAM | PPI-TM | 6 + 5 | CN | 10/85 | WG | 98/98 |
| | | | | | | JG | 98/98 |
| 33 | VERNAM | IF | 1.25 + 5 | BA | 40/85 | | |
| | | IF | 6 + 5 | CN | 0/90 | | |
| | EPTAM | PPI-TM | 5 + 5 | CN | 0/85 | WG | 98/98 |

TABLE II-continued

| | | | | | | | FT | 98/98 |
|---|---|---|---|---|---|---|---|---|
| 34 | VERNAM | IF | 6 + 5 | CN | 0/90 | | | |
| | EPTAM | PPI-TM | 5 + 0.5 | CN | 0/85 | | WG | 98/98 |
| | | | | | | | JG | 98/98 |
| 35 | VERNAM | IF | 1.25 + 5 | BA | 40/85 | | | |
| | | IF | 6 + 5 | CN | 30/90 | | | |
| | EPTAM | PPI-TM | 5 + 5 | CN | 0/85 | | WG | 98/98 |
| | | | | | | | JG | 98/98 |
| | VERNAM | PPI-TM | 1.25 + 5 | WH | 50/80 | | WG | 50/90 |
| 36 | VERNAM | IF | 6 + 5 | SOY | 50/65 | | | |
| | VERNAM | IF | 1.25 + 5 | MO | 30/100 | | | |
| | | IF | 1.25 + 5 | BA | 40/85 | | | |
| | | IF | 6 + 5 | CN | 20/90 | | | |
| | EPTAM | PPI-TM | 5 + 0.05 | CN | 0/85 | | WG | 90/98 |
| | | | | | | | JG | 75/98 |
| | RONEET | PPI-TM | 3 + 2 | MO | 0/80 | | WG | 100/100 |
| | | | | | | | FT | 100/100 |
| 38 | VERNAM | IF | 6 + 5 | CN | 60/95 | | | |
| | | IF | 6 + 5 | SOY | 50/60 | | | |
| 39 | VERNAM | IF | 6 + 5 | CN | 20/95 | | | |
| 40 | VERNAM | IF | 6 + 5 | SOY | 40/60 | | | |
| | | IF | 6 + 5 | CN | 50/95 | | | |
| 41 | VERNAM | IF | 6 + 5 | CN | 30/95 | | | |
| 42 | VERNAM | IF | 6 + 5* | CN | 35/95 | | | |
| | | IF | 6 + 5 | SOY | 40/60 | | | |
| 43 | VERNAM | IF | 6 + 5 | CN | 75/95 | | | |
| 44 | VERNAM | IF | 1.25 + 5 | BA | 45/75 | | | |
| | | IF | 6 + 5 | SOY | 20/40 | | | |
| 45 | VERNAM | IF | 1.25 + 5 | BA | 50/75 | | | |
| 46 | VERNAM | IF | 6 + 5 | CN | 65/90 | | | |

The compounds and compositions of this invention were employed in effective herbicidal compositions comprising the antidote and a thiolcarbamate herbicide as described hereinabove. The herbicidal compositions were tested in the above manner.

A preferred herbicidal compositions consists essentially of a thiolcarbamate herbicide and an antidotally effective amount of an antidote compound therefor corresponding to the formula described hereinabove, and known as 5-oxy or 5-thiomethyl substituted haloacyl oxazolidines.

The compositions of the present invention for the protection of cultivated crop plants comprise the active herbicidal compound and an antidote therefor selected from the above-described compounds. The compositions of herbicide and antidote can be prepared by conventional methods through the thorough mixing and grinding of the active herbicide agents and the antidote with suitable carriers and/or other distribution media, possibly with the addition of dispersion agents or solvents.

The antidote compounds and compositions of the present invention can be used in any convenient form. A solvent or inert carrier is not necessary in view of low volume spray technology which permits the use of neat technical grade materials as sprays. Thus, the antidote compounds and composition with the thiolcarbamate herbicide can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicide can be incorporated into the soil. Moreover, the crop seed itself can be treated with a non-phytotoxic quantity of the compound and planted into the soil which has been treated with herbicide, or untreated with the herbicide and subsequently treated with the herbicide. The addition of the antidote compound does not affect the herbicidal activity of the herbicide. The alternative methods of application have been exemplified in the above examples.

The amount of antidote compound present can range between about 0.001 to about 30 parts by weight of antidote compound described herein per each part by weight of herbicide. The exact amount of antidote compound will usually be determined on economic ratios for the most effective amount usable. It is understood that a non-phytotoxic, but effective quantity of antidote compound will be employed in the herbicidal compositions and methods described herein.

After treatment with the antidote and herbicide, there is obtained as a resultant thereof, soil which is novel in composition. Said soil is improved in its capability to grow crops and to offer weed control. Further, said soil treated with herbicide and antidote has the particular utility for allowing seeds of crops otherwise injured by the herbicide, to be planted and grown. The herbicide has its utility in controlling undesirable vegetation; the antidote compound decreases the injury from the herbicide upon the crop species, and the soil treated with herbicide and antidote compound provides an improved media to grow the crop in the presence of an otherwise injurious herbicide.

In the utility of the present antidote compounds and improved herbicide system, the thiolcarbamate can be applied to the soil. Application of the herbicide to the soil can take place by pre-plant incorporation. In conjunction with the prior application of the herbicide employing the present invention crop seeds are planted. Seed planting is followed by application of the antidote as a pre-emergence surface application. This sequence of application of herbicide, seed planting and antidote is unusual and fully effective in decreasing injury to the plant crop, otherwise injured by the thiolcarbamate herbicide.

I claim:

1. A compound according to the formula

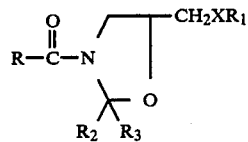

in which X is sulfur, R is haloalkyl, $R_1$ is alkyl and $R_2$ and $R_3$ are each lower alkyl.

2. A compound according to claim 1 in which R is monochloromethyl, $R_1$ is ethyl and $R_2$ and $R_3$ are each methyl.

3. A compound according to claim 1 in which R is 1,2-dibromoethyl, $R_1$ is ethyl and $R_2$ and $R_3$ are each methyl.

4. A compound according to claim 1 in which R is 2-bromoethyl, $R_1$ is ethyl and $R_2$ and $R_3$ are each methyl.

5. A compound according to claim 1 in which R is 1-chloroethyl, $R_1$ is ethyl and $R_2$ and $R_3$ are each methyl.

6. A compound according to claim 1 in which R is dichloromethyl, $R_1$ is ethyl and $R_2$ and $R_3$ are each methyl.

7. A compound according to claim 1 in which R is 1,2-dibromoheptyl, $R_1$ is ethyl and $R_2$ and $R_3$ are each ethyl.

8. A compound according to claim 1 in which X is sulfur, $R_1$ is alkyl, R is alkylthio and $R_2$ and $R_3$ are each lower alkyl.

9. A compound according to claim 8 in which $R_1$ is ethyl, R is ethylthio and $R_2$ and $R_3$ are each methyl.

10. A compound according to claim 1 in which X is oxygen, $R_1$ is alkyl, R is alkylthio and $R_2$ and $R_3$ are each lower alkyl.

11. A compound according to claim 1 in which X is sulfur; $R_1$ is alkyl, R is p-tolylsulfonamido and $R_2$ and $R_3$ are each lower alkyl.

* * * * *